United States Patent
Marks et al.

(10) Patent No.: US 6,274,752 B1
(45) Date of Patent: *Aug. 14, 2001

(54) ORGANO-LEWIS ACID AS COCATALYST FOR CATIONIC HOMOGENEOUS ZIEGLER-NATTA OLEFIN POLYMERIZATIONS

(75) Inventors: Tobin J. Marks, Evanston, IL (US); You-Xian Chen, Midland, MI (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/329,431

(22) Filed: Jun. 10, 1999

Related U.S. Application Data

(60) Continuation-in-part of application No. 09/220,741, filed on Dec. 23, 1998, now Pat. No. 6,087,460, which is a division of application No. 08/800,548, filed on Feb. 18, 1997, now Pat. No. 5,856,256
(60) Provisional application No. 60/011,920, filed on Feb. 20, 1996.

(51) Int. Cl.[7] .................................................. C07F 17/00
(52) U.S. Cl. ............................... 556/53; 556/7; 502/152; 502/102; 502/103; 502/104; 502/117; 526/134; 526/170; 526/172; 526/543
(58) Field of Search .................................... 526/134, 170, 526/172, 348, 943; 568/606, 617; 502/152, 102, 103, 104, 117; 556/7, 53

(56) References Cited

U.S. PATENT DOCUMENTS

| | | | |
|---|---|---|---|
| 3,950,435 | 4/1976 | Takahashi et al. | 260/613 R |
| 3,966,453 | 6/1976 | Takahashi et al. | 71/105 |
| 5,064,802 | 11/1991 | Stevens et al. | 502/102 |
| 5,296,433 | 3/1994 | Siedle et al. | 502/103 |
| 5,300,598 | 4/1994 | Marks et al. | 526/160 |

(List continued on next page.)

FOREIGN PATENT DOCUMENTS

| | | |
|---|---|---|
| 0416815 | 3/1991 | (EP) . |
| 0427697 | 5/1991 | (EP) . |
| 0468651 | 1/1992 | (EP) . |
| 0561479 | 9/1993 | (EP) . |
| 0573403 | 12/1993 | (EP) . |
| 9729845 | 8/1997 | (WO) . |
| 9735893 | 10/1997 | (WO) . |
| 9832776 | 7/1998 | (WO) . |
| 9841530 | 9/1998 | (WO) . |
| 9850392 | 11/1998 | (WO) . |

OTHER PUBLICATIONS

Marks, Tobin, J., "Surface–Bound Metal Hydrocarbyls. Organometallic Connections between Heterogenous and Homogeneous Catalysts", Accounts of Chemical Research, 1992, vol. 25, No. 2, pp. 57–65.

Yang et al., "Cationic Zirconocene Olefin Polymerization Catalysts Based on the Organo–Lewis Acid Tris(pentafluorophenyl)borane. A Synthetic, Structural, Solution Dynamic, and Polymerization Catalytic Study", J. Am. Chem. Soc., 1994, No. 116, pp. 10015–10031.

(List continued on next page.)

Primary Examiner—David W. Wu
Assistant Examiner—Caixia Lu
(74) Attorney, Agent, or Firm—Sieberth & Patty, L.L.C.

(57) ABSTRACT

Organo-Lewis acids of the formula BR'R"$_2$ wherein B is boron, R' is fluorinated biphenyl, and R" is a fluorinated phenyl, fluorinated biphenyl, or fluorinated polycyclic fused ring group, and cationic metallocene complexes formed therewith. Such complexes are useful as polymerization catalysts.

40 Claims, 6 Drawing Sheets

U.S. PATENT DOCUMENTS

| | | | |
|---|---|---|---|
| 5,330,948 | 7/1994 | Marks et al. | 502/102 |
| 5,332,706 | 7/1994 | Nowlin et al. | 502/107 |
| 5,391,661 | 2/1995 | Naganuma et al. | 502/102 |
| 5,391,789 | 2/1995 | Rohrmann | 556/11 |
| 5,455,366 | 10/1995 | Rohrmann et al. | 556/8 |
| 5,468,708 | 11/1995 | Cooley et al. | 502/162 |
| 5,473,028 | 12/1995 | Nowlin et al. | 526/114 |
| 5,486,632 | 1/1996 | Devore et al. | 502/103 |
| 5,496,960 | 3/1996 | Piers et al. | 556/7 |
| 5,498,581 | 3/1996 | Welch et al. | 502/102 |
| 5,500,398 | 3/1996 | Marks et al. | 502/103 |
| 5,502,017 | 3/1996 | Marks et al. | 502/103 |
| 5,539,068 | 7/1996 | Devore et al. | 526/126 |
| 5,550,265 | 8/1996 | Castellanos et al. | 556/58 |
| 5,554,775 | 9/1996 | Krishnamurti et al. | 556/7 |
| 5,582,764 | 12/1996 | Nakashima et al. | 252/299.61 |
| 5,596,054 | 1/1997 | Takeuchi | 502/103 |
| 5,599,761 | 2/1997 | Turner | 502/152 |
| 5,602,067 | 2/1997 | Nowlin et al. | 502/104 |
| 5,721,183 | 2/1998 | Neithamer | 502/103 |
| 5,728,784 | 3/1998 | Po' et al. | 502/102 |
| 5,753,578 | 5/1998 | Santi et al. | 556/53 |
| 5,756,611 | 5/1998 | Etherton et al. | 526/127 |
| 5,786,495 | 7/1998 | Resconi et al. | 556/11 |
| 5,856,256 | 1/1999 | Marks et al. | 502/152 |

OTHER PUBLICATIONS

Beck et al., "Binuclear Zirconocene Cations with $\mu$-CH$_3$-bridges in Homogeneous Ziegler-Natta Catalyst Systems", Journal of Molecular Catalysis A: Chemical, vol. 111, 1996, pp. 67–79.

Bochmann et al., "Monomer-Dimer Equilibria in Homo-and Heterodinuclear Cationic Alkylzirconium Complexes and Their Role in Polymerization Catalysis", Angew Chem. Int. Ed. Engl., 1994, vol. 33, No. 15/16, pp. 1634–1637.

Chen et al., ""Constrained Geometry" Dialkyl Catalysts Efficient Syntheses, C–H Bond Activation Chemistry, Monomer-Dimer Equilibration, and α-Olefin Polymerization Catalysis", Organometallics, 1997, vol. 16, No. 16, pp. 3649–3657.

Chen et al., "Sterically Encumbered (Perfluoroaryl) Borane and Aluminate Cocatalysts for Tuning Cation-Anion Ion Pair Structure and Reactivity in Metallocene Polymerization Processes. A Synthetic, Structural, and Polymerization Study", J. Am. Chem. Soc., 1998, vol. 120, No. 25, pp. 6287–6305.

Chen et al., "Organo-Lewis Acids as Cocatalysts in Cationic Metallocene Polymerization Catalysis. Unusual Characteristics of Sterically Encumbered Tris(perfluorobiphenyl)borane", J. Am. Chem. Soc. 1996, vol. 118, No. 49, pp. 12451–12452.

Fenton et al., "Perfluorophenyl Derivatives of the Elements II. (Pentafluorophenyl)lithium, A Source of $_2$-Substituted Nonafluorobiphenyls", J. Organometal Chem., vol. 2, 1964, pp. 437–446.

Jia et al., "Cationic Metallocene Polymerization Catalysts Based on Tetrakis(pentafluorphenyl)borate and Its Derivatives. Probing the Limits of Anion "Noncoordination" via a Synthetic, Solution Dynamic, Structural, and Catalytic Olefin Polymerization Study", Orgmet., 1997, vol. 16, No. 5, pp. 842–857.

Li et al., "New Organo-Lewis Acids. Tris($\beta$-perfluoronaphthyl)borane (PNB) as a Highly Active Cocatalyst for Metallocene-Mediated Ziegler-Natta α-Olefin Polymerization", Organometallics, 1998, vol. 17, No. 18, pp. 3996–4003.

Piers et al., "Pentafluorophenylboranes: From Obscurity to Applications", Chemical Society Reviews, 1997, vol. 26, pp. 345–354.

Siedle et al., "How coordinating are Non–coordinating Anions?", Macromol. Symp., 1995, vol. 89, pp. 299–305.

Yang et al., "Models for Organometallic Molecule–Support Complexes. Very Large Counterion Modulation of Cationic Actinide Alkyl Reactivity", Organometallics, 1991, vol. 10, pp. 840–842.

ORGANO-LEWIS ACID AS COCATALYST FOR CATIONIC HOMOGENEOUS ZIEGLER-NATTA OLEFIN POLYMERIZATIONS

REFERENCE TO RELATED APPLICATIONS

This application is a continuation-in-part of our prior application Ser. No. 09/220,741, filed Dec. 23, 1998, now U.S. Pat. No. 6,087,460, which is a division of application Ser. No. 08/800,548, filed Feb. 18, 1997, now U.S. Pat. No. 5,856,256, issued Jan. 5, 1999, which in turn claims priority of U.S. provisional application No. 60/011,920, filed Feb. 20, 1996.

This invention was made with Government support under Contract No. DE-FG02-86ER13511 awarded by the Department of Energy. The Government has certain rights in this invention.

BACKGROUND OF THE INVENTION

This invention relates to the compositions of matter useful as catalysts, to a method for preparing these catalysts and to a method for polymerization utilizing the catalysts.

The use of soluble Ziegler-Natta type catalysts in the polymerization of olefins is well known in the prior art. In general, such systems include a Group IV-B metal compound and a metal or metalloid alkyl cocatalyst, such as aluminum alkyl cocatalyst. More broadly, it may be said to include a mixture of a Group I-III metal alkyl and a transition metal complex from Group IVB-VB metals, particularly titanium, zirconium, or hafnium with aluminum alkyl cocatalysts.

First generation cocatalyst systems for homogeneous metallocene Ziegler-Natta olefin polymerization, alkylaluminum chlorides ($AlR_2Cl$), exhibit low ethylene polymerization activity levels and no propylene polymerization activity. Second generation cocatalyst systems, utilizing methyl aluminoxane (MAO), raise activities by several orders of magnitude. In practice however, a large stoichiometric excess of MAO over catalyst ranging from several hundred to ten thousand must be employed to have good activities and stereoselectivities. Moreover, it has not been possible to isolate characterizable metallocene active species using MAO. The third generation of cocatalyst, $B(C_6F_5)_3$, proves to be far more efficient while utilizing a 1:1 catalyst-cocatalyst ratio. Although active catalyst species generated with $B(C_6F_5)_3$, are isolable and characterizable, the anion $MeB(C_6F_5)_3^{\ominus}$, formed after $Me^{\ominus}$ abstraction from metallocene dimethyl complexes is weakly coordinated to the electron-deficient metal center, thus resulting in a drop of certain catalytic activities. The recently developed $B(C_6F_5)_4^{\ominus}$ type of non-coordinating anion exhibits some of the highest reported catalytic activities, but such catalysts have proven difficult to obtain in the pure state due to poor thermal stability and poor crystallizability, which is crucial for long-lived catalysts and for understanding the role of true catalytic species in the catalysis for the future catalyst design. Synthetically, it also takes two more steps to prepare such an anion than for the neutral organo-Lewis acid.

SUMMARY OF THE INVENTION

Accordingly, it is an object of the subject invention to prepare and utilize a new class of olefin polymerization catalysts.

A further object of the subject invention is a catalyst which permits better control over molecular weight, molecular distribution, stereoselectivity, and comonomer incorporation.

Another object of the subject invention is a Ziegler-Natta type catalyst system which reduces the use of excess cocatalyst and activates previously unresponsive metallocenes.

These and other objects are attained by the subject invention whereby in one embodiment, a strong organo-Lewis acid, such as perfluorobiphenylborane (PBB) is utilized as a highly efficient cocatalyst for metallocene-mediated olefin polymerization and as a catalyst for a ring opening polymerization of THF. PBB can be synthesized in much higher yield than $B(C_6F_5)_3$ and the anion generated with PBB is non-coordinating instead of weakly coordinating as in the case of $B(C_6F_5)_3$. Thus, the former exhibits higher catalytic activities and can activate previously unresponsive metallocenes. The catalytically active species generated with PBB are isolable, X-ray crystallographically characterizable instead of the unstable, oily residues often resulting in the case of $B(C_6F_5)_4^{\ominus}$. In addition, PBB exhibits even higher catalytic activities in most cases.

In one embodiment of the subject invention a strong organo-Lewis acid, such as perfluorobiphenylborane (PBB), is utilized to synthesize stoichiometrically precise, isolable/crystallographically characterizable, highly active "cation-like" metallocene polymerization catalysts. The biphenyl groups of PBB may be connected to the boron at the meta, para, or ortho position.

PBB reacts with early transition metal or actinide alkyls to yield highly reactive cationic complexes: $(CpCp'MR)^{\oplus}(RBR'R''_2)^{\ominus}$
where
$CpCp'=C_5H_nR_{5-n}$ (n is 0–5), indenyl, allyl, benzyl, $C_5H_nR_{4-n}XNR$ (n is 0–4);
M=early transition metal or actinide, e.g., Ti, Zr, Hf, Th, U;
$X=R'''_2Si$, where R''' is an alkyl or aryl group ($C \leq 10$);
R, R'''=alkyl, benzyl, or aryl group ($C \leq 20$), hydride, silyl;
B=boron
R'=fluorinated biphenyl
R''=fluorinated phenyl, fluorinated biphenyl, or fluorinated polycyclic fused rings such as naphthyl, anthracenyl, or fluorenyl.

As a specific example of the above, the reaction of PBB with a variety of zirconocene dimethyl complexes proceeds rapidly and quantitatively to yield, after recrystallization from hydrocarbon solvents, the catalytic complex of Eq. 1.

(Eq.1)

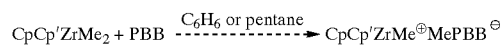

$$CpCp'ZrMe_2 + PBB \xrightarrow{C_6H_6 \text{ or pentane}} CpCp'ZrMe^{\oplus}MePBB^{\ominus}$$

Such catalytic complexes have been found to be active homogeneous catalysts for α-olefin polymerization and, more particularly, the polymerization, copolymerization or oligopolymerization of ethylene, α-olefins, dienes and acetylenic monomers, as well as intramolecular C—H activation.

The cocatalyst of the subject invention may be referred to as $BR'R''_2$, where B=boron; R' and R'' represent at least one and maybe more fluorinated biphenyls or other polycyclic groups, such as naphthyl. Two of the biphenyls may be substituted with a phenyl group. Both the biphenyls and the phenyl groups should be highly fluorinated, preferably with only one or two hydrogens on a group, and most preferably, as in PBB with no hydrogens and all fluorines.

BRIEF DESCRIPTION OF THE DRAWINGS

The cocatalyst system of the subject invention can be better understood with reference to the drawings wherein.

DETAILED DESCRIPTION OF THE INVENTION

The reaction of perfluorobiphenylborane with a variety of zirconocene and other actinide or transition metal dimethyl complexes proceeds rapidly and quantitatively at room temperature in noncoordinating solvents to yield, after recrystallization, complexes. This catalyst activation reaction may be used in the polymerization, copolymerization, oligomerization and dimerization of α-olefins. In addition, the catalyst of the subject invention may be used in conjunction with aluminum alkyls, aluminum aryls, ($AlR_3$, R=Et, Me, Ph, naphthyl) or methyl alumoxane $(Al(CH_3)O)_n$ for increased polymer yields.

Figure 1:
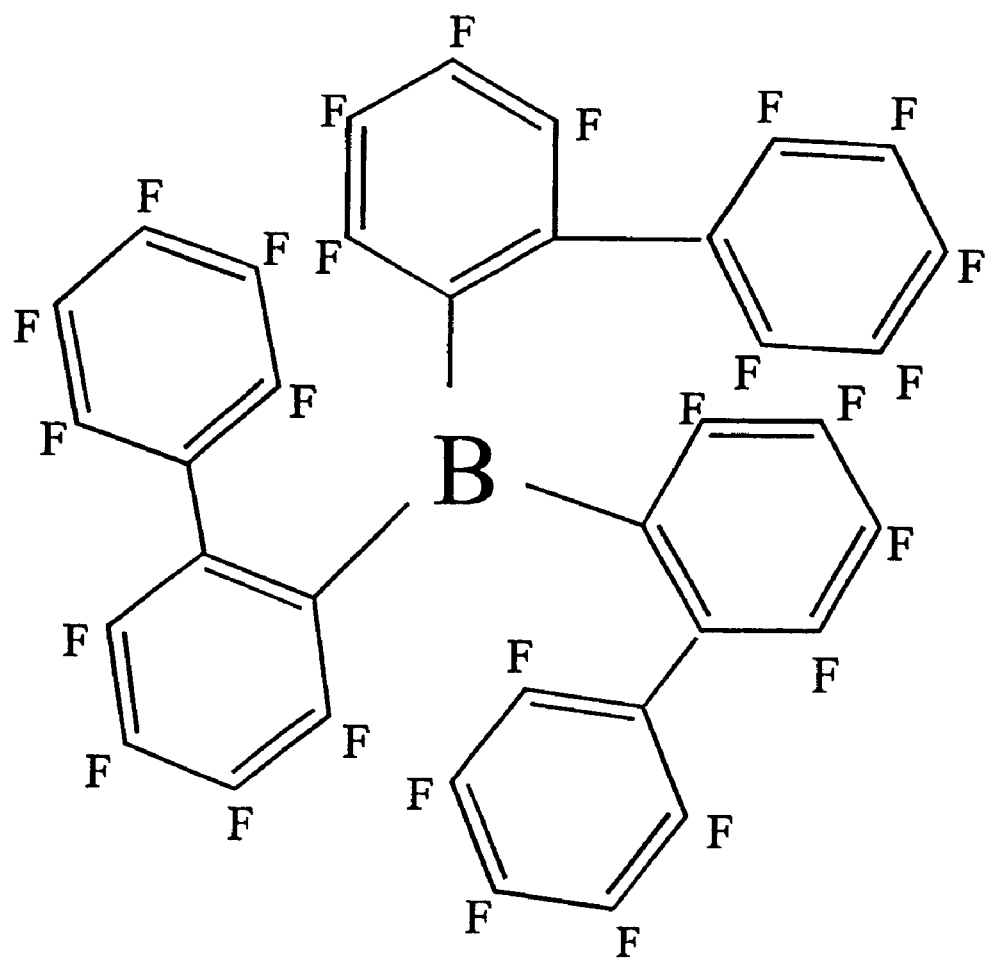
FIG. 1 is a structural depiction of PBB.
Figure 2:
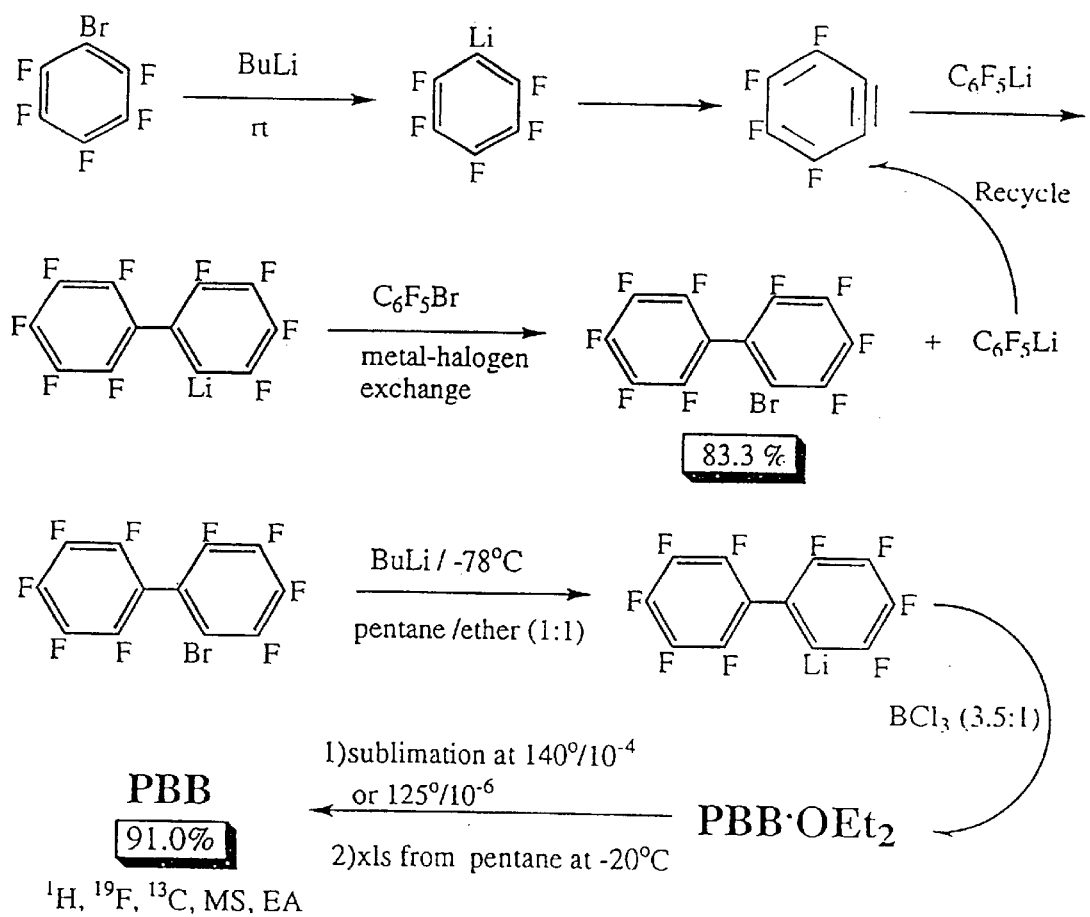
FIG. 2 is a reaction pathway for the synthesis of PBB.
Figure 3:
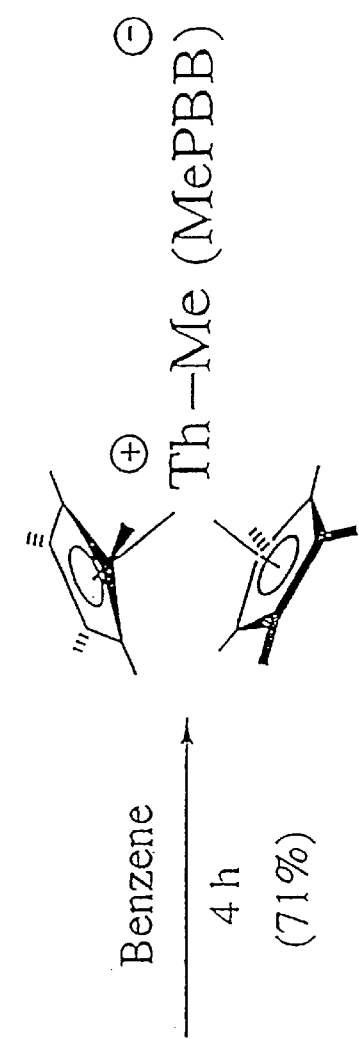
FIG. 3 shows the reaction pathway for a catalyst system according to the subject invention.
Figure 3:
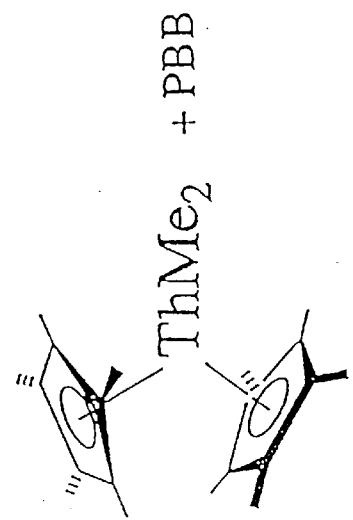

PBB (FIG. 1) has been synthesized in quantitative yields of 91% as compared to the 30–50% yields experienced with $B(C_6F_5)_3$, currently a very important Lewis acidic cocatalyst in industry (FIG. 2). The Lewis acidity of PBB has been shown to be much greater than that of $B(C_6F5)_3$ by comparative reactions of $Cp*_2ThMe_2$ with $B(C_6F_5)_3$ and PBB ($Cp*=C_5Me_5$). The former reagent does not effect $Me^\ominus$ abstraction, while the latter gives the catalyst shown in FIG. 3. The reaction of PBB with a bis-Cp type of dimethyl zirconocenes forms a dinuclear methyl-bridged zirconocene cation such as

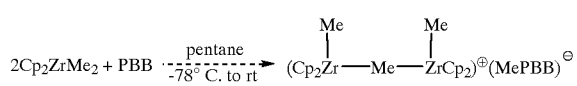

(1:1 or 2:1)
where
 $Cp=C_5H_5$
 $Cp=C_5H_3Me_2$ or
 $Cp=C_5Me_5$
and a hydride-bridged analog such as

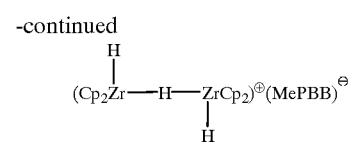

where
 $Cp=C_5H_5$ or
 $Cp=C_5H_3Me_2$

More particularly, reaction of PBB with group 4 and Th methyls proceeds cleanly to yield cationic complexes such as set forth below.

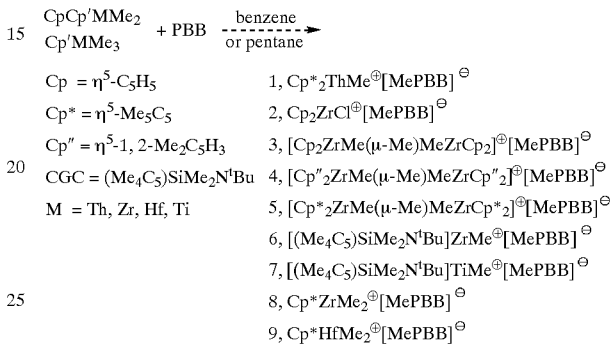

For ethylene polymerization, catalytic activities of dinuclear cations generated from PBB are greater than those of monomeric cations generated from $B(C_6F_5)_3$ presumably because $(MePBB)^\ominus$ is a non-coordinating anion as compared to the weakly coordinating anion $MeB(C_6F_5)_3$. The dinuclear cations have also been found to catalyze the rapid ring-opening polymerization of THF to produce poly (tetrahydrofuran), an important thermoplastic elastomer and artificial leather. Monomeric zirconocene cations have also been generated in situ by the reaction of $Cp_2ZrMe_2$ and PBB at 60° C.:

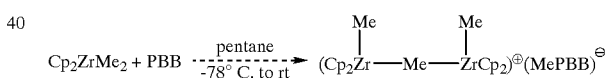

where $Cp=C_5H_5$, $C_5H_3Me_2$, or $C_5Me_5$, or

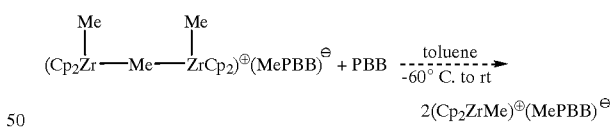

These attempts show very high activities for olefin polymerization, and identify $(MePBB)^\ominus$ to be a truly non-coordinating anion. The polymerization data with metallocene cations having various anions are summarized in Table 1.

TABLE 1

| | | | Polymerization Data | | | | | |
|---|---|---|---|---|---|---|---|---|
| Entry No. | Catalyst | μmol of cat | Conditions | Monomer(s)[a] | Polymer yield (g) | Activity[b] | $M_{wd}$[c] $(10^{-3})$ | $M_w/M_n$ | Remarks |
| 1 | $(Cp_2ZrMe)_2Me^\oplus$ $MePBB^\ominus$ | 15 | 100 mL toluene 25° C., 40 s | ethylene | 0.80 | 4.80 × 10⁶ | 559 | 3.06 | |

TABLE 1-continued

Polymerization Data

| Entry No. | Catalyst | μmol of cat | Conditions | Monomer(s)[a] | Polymer yield (g) | Activity[b] | $M_{wd}^{c}$ $(10^{-3})$ | $M_w/M_n$ | Remarks |
|---|---|---|---|---|---|---|---|---|---|
| 2 | $Cp_2ZrMe^{\oplus}$ $MeB(C_6F_5)_3^{\ominus}$ | 15 | 100 mL toluene 25° C., 60 s | ethylene | 1.00 | $4.00 \times 10^6$ | 124 | 2.03 | |
| 3 | $(CP''_2ZrMe)_2Me^{\oplus}$ $MePBB^{\ominus}$ | 15 | 100 mL toluene 25° C., 40 s | ethylene | 1.30 | $7.80 \times 10^6$ | 392 | 2.72 | |
| 4 | $Cp''_2ZrMe^{\oplus}$ $MeB(C_6F_5)_3^{\ominus}$ | 15 | 100 mL toluene 25° C., 60 s | ethylene | 1.50 | $6.00 \times 10^6$ | 321 | 1.42 | |
| 5 | $(Cp*_2ZrMe)_2Me^{\oplus}$ $MePBB^{\ominus}$ | 15 | 100 mL toluene 25° C., 60 s | ethylene | 1.07 | $4.30 \times 10^6$ | 370 | 2.28 | |
| 6 | $Cp*_2ZrMe^{\oplus}$ $MeB(C_6F_5)_3^{\ominus}$ | 15 | 100 mL toluene 25° C., 60 s | ethylene | 0.80 | $3.20 \times 10^6$ | 136 | 2.54 | |
| 7 | $Cp*TiMe^{\oplus}_2$ $MePBB^{\ominus}$ | 50 | 5 mL toluene 25° C., 15 min | styrene | 0.35 | $1.61 \times 10^6$ | 170 | 2.56 | [rrrr] > 98% |
| 8 | $Cp*ZrMe^{\oplus}_2$ $MePBB^{\ominus}$ | 50 | 5 mL toluene 25° C., 10 min | styrene | 1.45 | $1.00 \times 10^7$ | 27.6 | 2.63 | atactic |
| 9 | $Cp*HfMe^{\oplus}_2$ $MeB(C_6F_5)_3^{\ominus}$ | 50 | 5 mL toluene 25° C., 15 min | styrene | 0.69 | $3.17 \times 10^6$ | 24.8 | 2.98 | atactic |
| 10 | $Cp*HfMe^{\oplus}_2$ $MePBB^{\ominus}$ | 50 | 5 mL toluene 25° C., 15 min | styrene | 1.16 | $5.33 \times 10^6$ | 22.9 | 2.78 | atactic |
| 11 | $Cp*TiMe^{\oplus}_2$ $MeB(C_6F_5)_3^{\ominus}$ | 50 | 25 mL toluene 25° C., 5 min | ethylene 1-hexene | 0.70 | $1.70 \times 10^5$ | 848 | 23.7 | 39.5% hexene incorporation |
| 12 | $Cp*TiMe^{\oplus}_2$ $MePBB^{\ominus}$ | 50 | 25 mL toluene 25° C., 5 min | ethylene 1-hexene | 4.51 | $1.08 \times 10^6$ | 151 | 4.32 | 43.6% hexene incorporation |
| 13 | $CGCZrMe^{\oplus}$ $MeB(C_6F_5)_3^{\ominus}$ | 15 | 100 mL toluene 25° C., 20 min | ethylene | 0 | — | — | — | |
| 14 | $CGCZrMe^{\oplus}$ $MePBB^{\ominus}$ | 15 | 100 mL toluene 25° C., 4 min | ethylene | 1.56 | $1.56 \times 10^6$ | 7.69 | 2.78 | |
| 15 | $CGCTiMe^{\oplus}$ $MeB(C_6F_5)_3^{\ominus}$ | 15 | 100 mL toluene 25° C., 10 min | ethylene | 0.21 | $8.40 \times 10^4$ | 1058 | 9.54 | |
| 16 | $CGCTiMe^{\oplus}$ $MePBB^{\ominus}$ | 15 | 100 mL toluene 25° C., 40 s | ethylene | 0.83 | $4.98 \times 10^6$ | 305 | 2.56 | |
| 17 | $CGCZrMe^{\oplus}$ $MeB(C_6F_5)_3^{\ominus}$ | 50 | 25 mL toluene 25° C., 15 min | ethylene | 0 | — | — | — | |
| 18 | $CGCZrMe^{\oplus}$ $MePBB^{\ominus}$ | 50 | 25 mL toluene 25° C., 15 min | ethylene 1-hexene | 6.97 | $5.58 \times 10^5$ | 10.0 | 2.68 | 33.6% hexene incorporation |
| 19 | $CGCTiMe^{\oplus}$ $MeB(C_6F_5)_3^{\ominus}$ | 25 | 25 mL toluene 25° C., 10 min | ethylene 1-hexene | 0.05 | $1.20 \times 10^4$ | | | 63.2% hexene incorporation |
| 20 | $CGCTiMe^{\oplus}$ $MePBB^{\ominus}$ | 25 | 25 mL toluene 25° C., 10 min | ethylene 1-hexene | 1.95 | $4.68 \times 10^5$ | 105 | 1.86 | 65.3% hexene incorporation |

[a]1 atm ethylene pressure; 17.4 mmol of styrene, & 44.5 mmol of 1-hexene.
[b]g polymer/[(mol of cationic metallocene).atm.h], except in entries 7–10: polystyrene/[(mol catalyst).(mol monomer).h] (reproducibility between runs ≈ 10~15%).
[c]GPC relative to polystyrene standards.

Figures 4, 5:
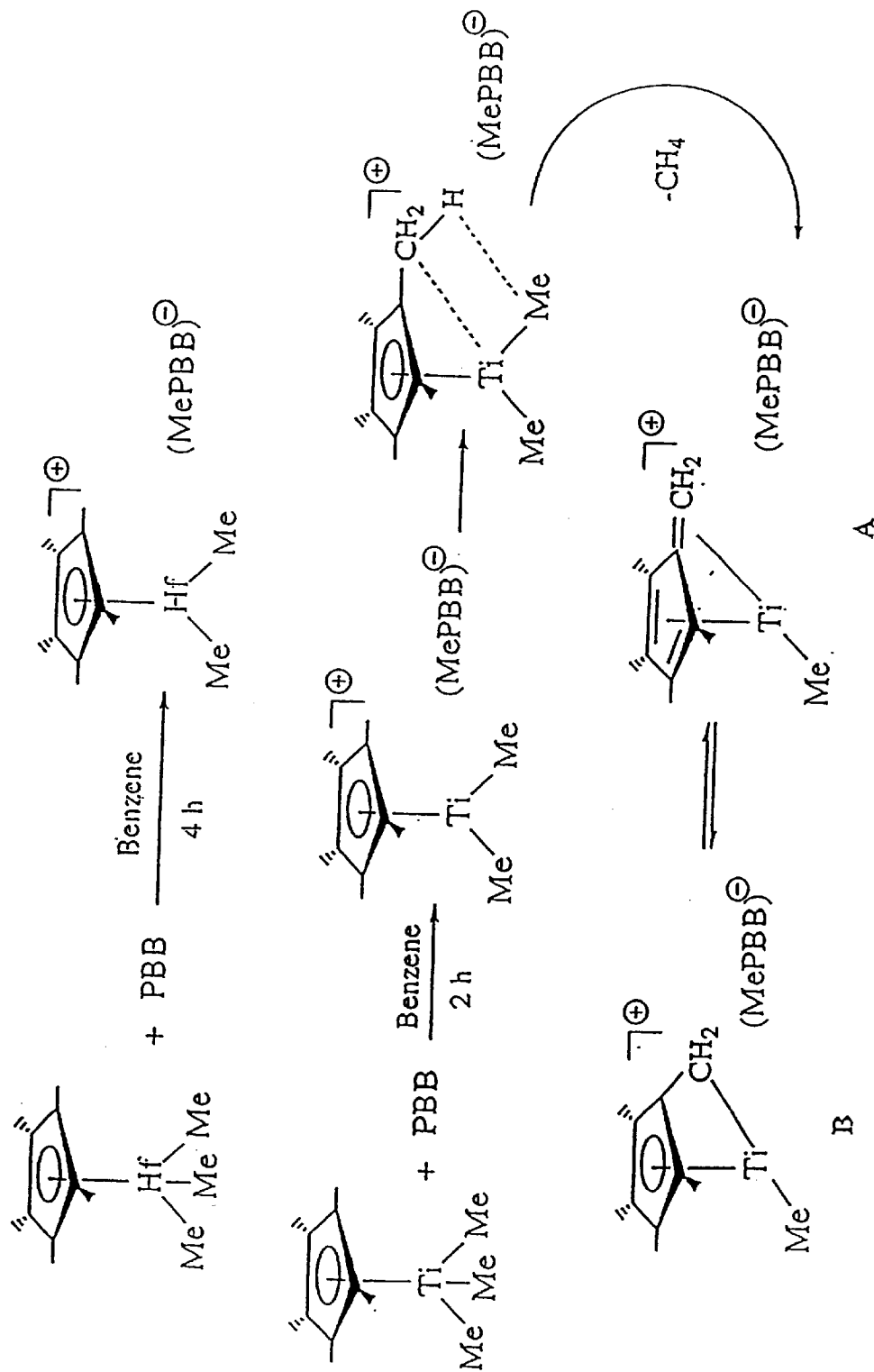
FIG. 4 shows the reaction pathway for a second catalyst system according to the subject invention.
FIG. 5 shows the reaction pathway for a third catalyst system according to the subject invention.
Figure 6:
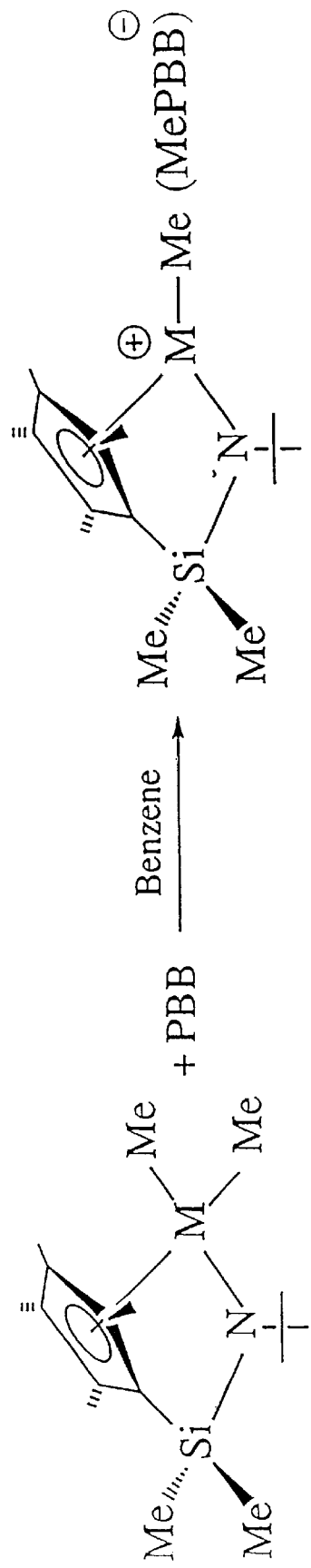
FIG. 6 shows the reaction pathway for a fourth catalyst system according to the subject invention.
Figure 7:
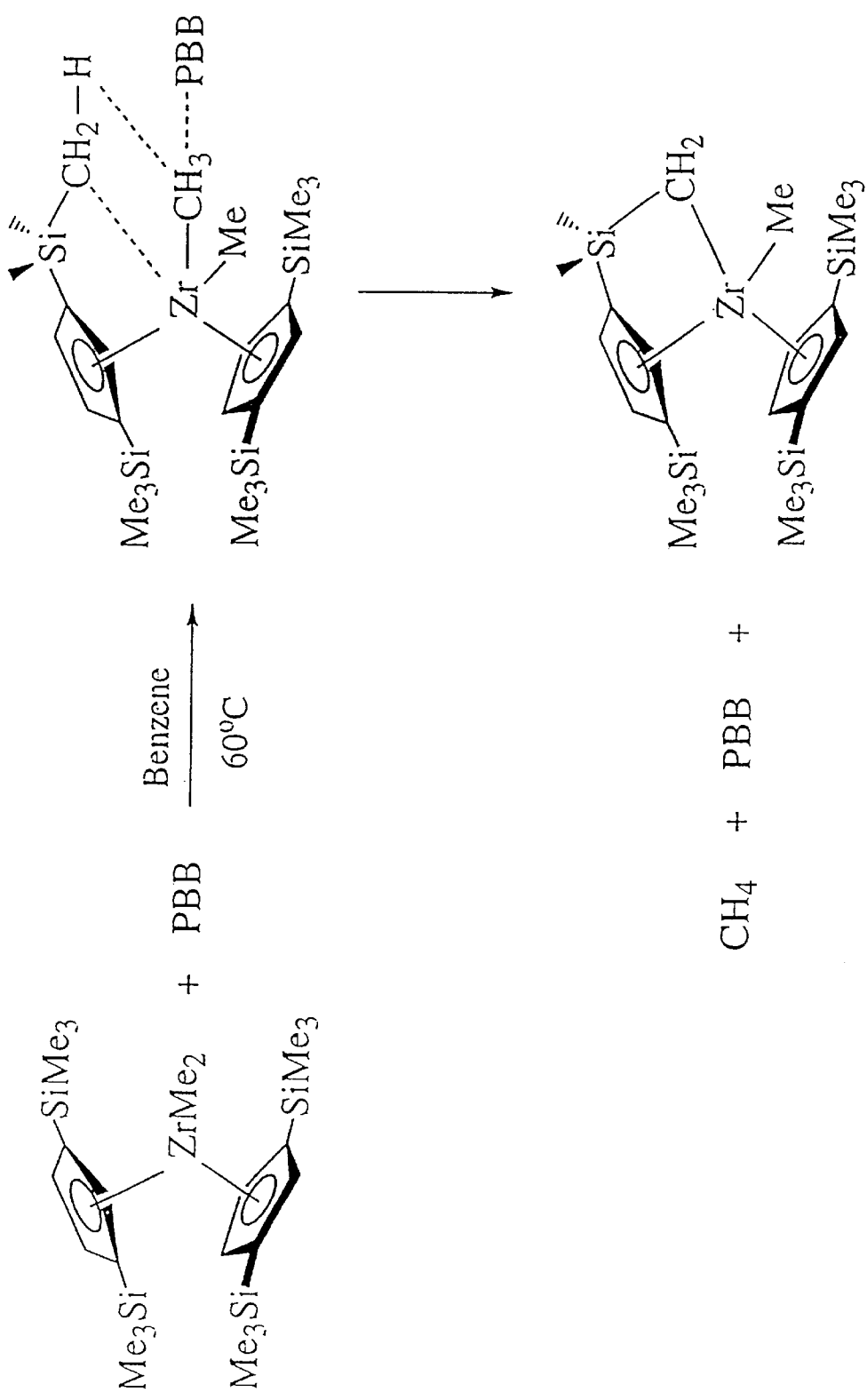
FIG. 7 shows the reaction pathway for a fifth catalyst system according to the subject invention.

Other types of cationic metallocene catalyst systems can also be created with PBB. Metallocene cations of mono-Cp type (FIGS. 4 and 5) have been formed by the reaction of mono-pentamethyl Cp trimethyl group IV complexes with PBB. These are very good syndiospecific styrene polymerization catalysts. Constrained geometry types of zirconocene and titanocene cations such as those in FIG. 6 where m=Zr, Ti, are readily produced by the reaction of the corresponding dimethyl metallocenes with PBB. They are highly naked cations and much more active catalysts than those generated with $B(C_6F_5)_3$.

EXAMPLE 1
Synthesis of Perfluorobiphenylborane (PBB)

n-Butyllithium (1.6 M in hexanes, 25 mL, 40 mmol) was added dropwise to bromopentafluorobenzene 18.0 g, 9.1 mL, 72.9 mmol) in 100 mL of diethyl ether over a cold-water bath. The mixture was then stirred for a further 12 h at room temperature. Removal of solvent followed by vacuum sublimation at 60–65° C./$10^{-4}$ torr gave 12.0 g of 2-bromononafluorobiphenyl as a white crystalline solid: yield 83.3%. The dangerous and explosive nature of $C_6F_5Li$-ether solutions in this preparation can be avoided by (a) the use of excess of $C_6F_5Br$, (b) slow addition of n-butyllithium, (c) frequent change of the cold water bath, or use of a continuous flowing cold water bath.

To the above prepared 2-bromononafluorobiphenyl (5.0 g, 12.7 mmol) in a mixed solvent of 70 mL of diethyl ether and 70 mL of pentane was gradually added 8.0 mL of n-butyllithium (1.6 M in hexanes, 12.8 mmol) at −78° C. The mixture was stirred for an additional 2 h, and boron trichloride (4.0 mL, 1.0 M in hexanes, 4.0 mmol) was then quickly added by a syringe. The mixture was left at −78° C. for 1 h and the temperature was then allowed to slowly rise to room temperature. A suspension resulted after stirring an additional 12 h. It was filtered to give a yellow solution, and the solvent of the filtrate was removed in vacuo. The resulting pale yellow powder was sublimed at 140° C./$10^{-4}$ torr or 125° C./$10^{-6}$ torr to produce a light yellow crystalline solid as an ether-free crude product. Recrystallization from pentane at −20° C. gave 3.5 g of the pure PBB as a white crystalline solid: yield 91.0%. Analytical and spectroscopic data for PBB are as follows. $^{19}$F NMR ($C_6D_6$, 23° C.): δ−120.08 (s, br, 3 F, F-3), −132.09 (s, br, 3 F, F-6), −137.66 (s, br, 6 F, F-2'/F-6'), −143.31 (t, $^3J_{F-F}$=21.4 Hz, 3 F, F-4), −149.19 (t, $^3J_{F-F}$=21.7 Hz, 3 F. F-4'), −150.56 (t, $^3J_{F-F}$=14.7 Hz, 3 F, F-5), 160.72 (s, br, 6 F, F-3'/F-5'). $^{13}$C NMR ($C_6D_6$, 23° C. ): δ150.92 (dd, $^1J_{C-F}$=251.8 Hz, $^2J_{C-F}$=10.1 Hz, 3 C), 146.35 (dd, $^1J_{C-F}$=254.3 Hz, $^2J_{C-F}$=12.1 Hz, 3 C), 144.26 (dd, $^1J_{C-F}$=258.1 Hz, $^2J_{C-F}$=10.5 Hz, 6 C), 143.50 (tt, $^1J_{C-F}$=265.4 Hz, $^2J_{C-F}$=12.0 Hz, 3 C), 141.98 (tt, $^1J_{C-F}$=

261.4 Hz, $^2J_{C-F}$=11.7 Hz, 3 C), 141.17 (tt, $^1J_{C-F}$=254.3 Hz, $^2J_{C-F}$=10.5 Hz, 3 C), 137.70 (tt, $^1J_{C-F}$=257.3 Hz, $^2J_{C-F}$=11.6 Hz, 6 C), 124.51 (d, $^2J_{C-F}$=11.7Hz, 3 C), 113.60 (d, $^2J_{C-F}$= 11.5 Hz, 3 C), 106.05 (s, br, 3 C). MS: parent ion at m/e 956. Anal. Calcd for $C_{36}BF_{27}$: C, 45.22; H, 0.00. Found: C, 45.44; H, 0.05.

EXAMPLE 2
Synthesis of $Cp*_2ThMe^{\oplus}$ $(MePBB)^{\ominus}$ $Cp*_2ThMe_2$ (0.106 g, 0.199 mmol) and PBB (0.191 g, 0.199 mmol) were in the glove box charged into a 25-mL reaction flask with a filter plug, and the flask was attached to the high vacuum line. Benzene (15 mL) was then vacuum-transferred into this flask at −78° C. The mixture was slowly allowed to warm to room temperature and stirred for 6 h. The solvent was removed, pentane (20 mL) was next vacuum-transferred into the flask, and the mixture was filtered after stirring. The white solid which collected was dried under vacuum to give 0.210 g of product: yield 70.9%. Analytical and spectroscopic data are as follows. $^1H$ NMR ($C_6D_6$, 23° C.): δ1.61 (s, 30 H, $C_5Me_5$), 0.62 (s, 3 H, Th—$CH_3$), −095 (s,br, 3 H, B—$CH_3$). $^{19}F$ NMR ($C_6D_6$, 23° C.): δ−124.57 (s, br, 3F), −138.10 (s, br, 3 F), −139.28 (d, $^3J_{F-F}$=21.4 Hz, 3 F), −139.74 (d, $^3J_{F-F}$=21.2 Hz, 3 F), −155.08 (t, $^3J_{F-F}$21.4 Hz, 3 F), −157.32 (t, $^3J_{F-F}$=22.0 Hz, 3 F), −162.20 (t, $^3J_{F-F}$=22.0 Hz, 3 F), −163.13 (t, $^3J_{F-F}$=22.0 Hz, 3 F), −163.90 (t, $^3J_{F-F}$=21.4 Hz, 3 F). $^{13}C$ NMR ($C_6D_6$, 23° C.): δ129.54 ($C_5Me_5$), 79.28 (Th—Me), 10.44 ($C_5Me_5$), 10.25 (B—Me). Anal. Calcd for $C_{58}H_{36}$ BF27 Th: C, 46.79; H, 2.44; N, 0.00. Found: C, 46.68; H, 2.24; N. 0.00.

EXAMPLE 3
Synthesis of $Cp_2Zr(Me)(\mu\text{-}Me)Me)ZrCp_2^{\oplus}(MePBB)^{\ominus}$(Cp= $C_5H_5$, $C_5H_3Me_2$, or $C_5Me_5$ $Cp_2ZrMe_2$ (0.398 mmol) and PBB (0.199 mmol) were loaded into a 25 mL-flask, which was then attached to the vacuum line. Pentane (20 mL) was then vacuum-transferred into this flask at −78° C. The mixture was slowly warmed to room temperature and stirred for an additional 2 h (Cp= $C_5H_5$), 15 h (Cp=$C_5H_3Me_2$) or 48 h (Cp=$C_5Me_5$). The resulting suspension was filtered, and the colored solids (light pink for $C_5H_5$, light yellow for $C_5H_3Me_2$ and yellow for $C_5Me_5$) were washed with a small amount of pentane and dried under vacuum: yields 90.3% ($C_5H_5$), 86.3% ($C_5H_3Me_2$) and 34.7% ($C_5Me_5$). Analytical and spectroscopic data for CP=$C_5H_5$ are as follows. $^1H$ NMR ($C_6D_6$, 23° C.): δ5.65 (s, 20H, $C_5H_5$), −0.04 (s, 6H, Zr—$CH_3$), −0.84 (s, br, 3H, B—$CH_3$), −1.15 (s, 3H, Zr—$CH_3$—Zr). $^{19}F$ NMR ($C_6D_6$, 23° C.): δ124.20 (d, $^3J_{F-}$=16.6 Hz, 3 F), −138.98 (d, $^3J_{F-F}$=20.3 Hz, 3 F), −139.20 (d, $^3J_{F-F}$=22.0 Hz, 3 F), −140.29 (d, $^3J_{F-F}$=24.5 Hz, 3 F), −155.15 (t, $^3J_{F-F}$=20.9 Hz, 3 F), −160.06 (t, $^3J_{F-F}$=22.3 Hz, 3 F), −162.79 (t, $^3J_{F-F}$=22.0 Hz, 3 F), −163.11 (t, $^3J_{F-F}$=21.5 Hz, 3 F), −163.97 (t, $^3J_{F-F}$=19.0 Hz, 3 F). $^{13}C$ NMR ($C_6D_6$, 23° C.): δ113.24 ($C_5H_5$), 38.88 (Zr—$CH_3$), 21.53 (B—$CH_3$), 15.80 (Zr—$CH$—Zr). Anal. Calcd for $C_{60}H_{32}BF_{27}Zr_2$: C, 49.39; H, 2.21; N, 0.00. Found: C, 48.97; H, 1.92; N 0.00.

Analytical and spectroscopic data for Cp=$C_5H_3Me_2$ are as follows. $^1H$ NMR ($C_7D_8$, 23° C. ): δ5.51 (t, $^3J_{H-H}$=2.8 Hz, 4H, $C_5H_3$ $Me_2$), 5.47 (t,$^3J_{H-H}$=3.2 Hz, 4H, $C_5H_3Me_2$), 5.18 (t, $^3J_{H-H}$=2.8 Hz, 4H, $C_5H_3Me_2$), 1.73 (s, 12H, $C_5H_3Me_2$) 1.51 (s, 12H, $C_5H_3MMe_2$), −0.26 (s, 6H, Zr—$CH_3$), −0.92 (s, br, 3H, B—$CH_3$), −1.50 (s, 3H, Zr—$CH_3$—Zr). $^{19}F$ NMR ($C_6D_6$, 23° C.): δ123.37 (d, $^3J_{F-F}$=15.3 Hz, 3F), −139.20 (d, $^3J_{F-F}$=24.0 Hz, 3 F), −139.62 (d, $^3J_{F-F}$=24.3 Hz, 3 F), −139.89 (d,$^3J_{F-F}$=24.0 Hz, 3 F), −155.81 (t, $^3J_{F-F}$=2.14 Hz, 3 F), −159.36 (t, $^3J_{F-F}$=22.3 Hz, 3 F), −163.22 (t, $^3J_{F-F}$=21.4 Hz, 3 F), −16.55 (t, $^3J_{F-F}$=22.0 Hz, 3 F), −164.20 (t, $^3J_{F-F}$=22.6 Hz, 3 F). $^{13}C$ NMR ($C_6D_6$, 23° C.): δ114.20 (d, $^1J_{CH}$=17.1 Hz, $C_5H_3Me_2$), 113.62 (s, $C_5H_3Me_2$), 112.80 (s, $C_5H_3Me_2$), 111.29 (d, $^1J_{CH}$165.7 Hz, $C_5H_3Me_2$), 106.57 (d, $^1J_{CH}$=173.8 Hz. $C_5H_3Me_2$), 41.63 (q, $^1J_{C-H}$118.4Hz, Zr—$CH_3$), 31.26 (q, $^1J_{CH}$=116.5 Hz, B—$CH_3$), 22.21 (q, $^1J_{CH}$=134.3 Hz, Zr—$CH_3$—Zr), 12.94 (q, $^1J_{CH}$=128.0 Hz, $C_5H_2Me_2$), 12.71 (q, $^1J_{CH}$=127.6 Hz. $C_5H_2Me_2$). Anal. Calcd for $C_{68}H_{48}BF_{27}Z_2$: C, 51,98; H, 3.08; N, 0.00. Found: C, 51.61; H, 3.00; N, 0.00.

Analytical and spectroscopic data for Cp=$C_5Me_5$ are as follows. $^1H$ NMR ($C_6D_6$, 23° C.): δ1.57 (s, 60H, $C_5Me_5$) −0.84 (s, br, 3H, B—$CH_3$). The bridging a terminal methyl groups are discrete at low temperature. $^1H$ NMR ($C_7D_8$, −13° C.): δ−0.19 (s, br, 6H. Zr—$CH_3$), −0.92 (s, br, 3H, B—$CH_3$), −2.42 (s, br, 3H, Zr—$CH_3$—Zr). $^{19}F$ NMR ($C_6D_6$, 23° C.): δ−123.11 (d, s, br, 3 F), −139.27 (d, $^3J_{F-F}$=20.3 Hz, 3 F), −139.67 (t, $3J_{F-F}$=25.1 Hz, 6F), −155.73 (t, $^3J_{F-F}$=20.9 Hz, 3 F), −160.91 (s, br, 3 F), −163.25 (t, $^3J_{F-F}$=21.7 Hz, 3 F), −163.56 (t, $^3J_{F-F}$=22.0 Hz, 3 F), −164.13 (t, $^3J_{F-F}$=21.4 Hz, 3 F). Anal. Calcd for $C_{80}H_{72}BF_{27}Zr_2$: C, 55.23; H, 4.17; N, 0.00. Found: C, 54.81; H, 3.98; N, 0.00.

EXAMPLE 4
Synthesis of $Cp_2Zr(H)(\mu\text{-}H)(H)ZrCp_2^{\oplus}(MePBB)^{\ominus}$; Cp=$C_5H$, $C_5H_3Me_2$ The procedure here is similar to that of Example 3, except that the reaction was carried out under 1 atm of $H_2$ for 15 h: yields 81.6% (Cp=$C_5H_5$, grey solid) and 75.6% (Cp= $C_5H_3Me_2$, orange solid). Analytical and spectroscopic data for Cp=$C_5H_5$ are as follows. $^1H$ NMR ($C_6D_6$, 58° C.): δ6.67 (s, br, 2H, Zr—H), 5.64 (s, 20H, $C_5H_5$), −0.81 (s, br, 3H, B—$CH_3$), −1.38 (s, br, 1H, Zr—H—Zr). The chemical shifts and splitting patterns of $^{19}F$ NMR are same as those of Example 3 (Cp=$C_5H_5$). Anal. Calcd for $C_{57}H_{26}BF_{27}Zr_2$: C, 48.31; H, 1.85; N, 0.00. Found: C, 47.90; H, 1.92; N, 0.00.

Analytical and spectroscopic data for Cp=$C_5H_3Me_2$ are as follows. $^1H$ NMR ($C_7D_8$, 23° C.): δ5.81 (m, 4H, $C_5H_3Me_2$), 5.50 (m, 4H, $C_5H_3Me_2$), 523 (m, 4H, $C_5H_3Me_2$). 1.65 (m, 24H, $C_5H_3Me_2$), 0.25 (s, br, 2H, Zr—H), −0.94 (s, br, 3H, B—$CH_3$), −1.52 (s, br, 1H, Zr—H—Zr). The chemical shifts and splitting patterns of $^{19}F$ NMR are same as those of Example 3 (Cp=$C_5H_3Me_2$). Anal. Calcd for $C_{65}H_{42}BF_{27}Zr_2$: C, 51.05; H, 2.77; N, 0.00. Found C, 51.07; H. −2.63; N. 0.00.

EXAMPLE 5
Preparation of $Cp_2ZrMe^{\oplus}(MePBB)^{\ominus}$

5(a) Cp=$C_5H_5$. In a J-Young NMR tube, a small amount of a mixture of $Cp_2ZrMe_2$ and PBB (1:1.2 molar ratio) was dissolved in $C_6D_6$). The NMR tube was then put in an NMR probe and heated at 60° C. After 0.5 h, $^1H$ NMR revealed the above monomeric species formed. The same structures were obtained by the reaction of the product of Example 3 with excess of PBB at 60° C. for 0.5 h. In a real polymerization test, these species were also generated in situ by mixing $Cp_2ZrMe_2$ and PBB at 60° C. for 0.5 h. $^1H$ NMR ($C_6D_6$, 60° C.) for: δ5.70 (s, 10H, $C_5H_5$), 0.14 (s, 3H, Zr—$CH_3$), −0.85 (s, br, 3H, B—$CH_3$). The $^{19}F$ NMR is similar to that of the corresponding dinuclear species of Example 3 (Cp=$C_5H_5$).

5(b) Cp=$C_5H_3Me_2$. The same procedure of Example 5(a) was used to prepare this species. In the polymerization test, the following was observed: $^1H$ NMR ($C_7D_8$, 60° C. ) for 8; δ5.68 (t, 3 J H—H=2.8 Hz, 4H, $C_5H_3Me_2$), 1.76 (s, $^3J_{H-H}$= 3.1 Hz, 4H, $C_5H_3Me_2$), 5.23 (t, $^3J_{H-H}$=2.8 Hz, 4H, $C_5H_3Me_2$), 1.76 (s, 6H, $C_5H_3Me_2$), 1.56 (s, 6H, $C_5H_3Me_2$), 0.17 (s, 3H, Zr—$CH_3$), −0.93 (s, br, 3H, B—$CH_3$). $^{19}F$ NMR of this species is similar to that of the corresponding dinuclear species of Example 3 (Cp=$C_5Me_5$). $^{13}C$ NMR ($C_7D_8$, 60° C. ): δ117.74 ($C_5H_3Me_2$), 112.14 ($C_5H_3Me_2$), 108.01 ($C_5H_3Me_2$), 42.11 (Zr—$CH_3$), 34.43 (B—$CH_3$), 12.63 ($C_5H_2Me_2$), 12.45 ($C_5H_2Me_2$).

5(c) Cp=$C_5Me_5$ The same procedure of Example 5(a) was used to prepare this species. In the polymerization test, the following was observed: $^1H$ NMR ($C_6D_6$, 60° C.): δ1.61 (s, 30H, $C_5Me_5$), 0.13 (s, 3H, Zr—$CH_3$), −0.86 (s, br, 3H, B—$CH_3$). $^{19}F$ NMR is similar to that of the corresponding dinuclear species of Example 3, Cp=$C_5Me_5$.

EXAMPLE 6
Synthesis of CpM(Me)$_2$⁺(MePBB)⁻; Cp=$C_5Me_5$

M=Ti. The catalyst product of FIG. 5 was generated in the NMR tube reaction by mixing $C_5Me_5TiMe_3$ and PBB at 1:1 molar ratio in $C_6D_6$ for 2 h. $^1H$ NMR ($C_6D_6$, 23° C.): δ9.03 (s, br, 2H, $CH_2$), 1.69 (s, 6H, $C_5Me_4$), 1.65 (s, 6H, $C_5Me_4$), 0.15 (s, 3H, Ti—$CH_3$), −0.82 (s, br, 3H, B—$CH_3$).

EXAMPLE 7
Synthesis of $Me_2Si(^tBuN)(C_5Me_4)MMe$⁺(MePBB)⁻

M=Zr. $Me_2Si(^tBuN)(C_5Me_4)MMe_2$ (0.199 mmol) and PBB (0.199 mmol) were treated in the same manner as in the preparation of Example 2 except for the different reaction times (2 h). This procedure yields 73.1% (yellow solid). Analytical and spectroscopic data are as follows. $^1H$ NMR ($C_7D_8$, 23° C.): δ1.73 (s, 3H, $C_5Me_4$), 1.69 (s, 3H, ($C_5Me_4$), 1.63 (s, 3H, $C_5Me_4$), 1.43 (s, 3H, $C_5Me_4$), 0.85 (s, 9H, N-$^tBu$), 0.28 (s, 3H, $SiMe_2$), 0.21 (s, 3H, $SiMe_2$), −0.48 (s, 3H, Zr—$CH_3$), −0.95 (s, br, 3H, B—$CH_3$). $^{19}F$ NMR ($C_7D_8$, 23° C.): δ124.20 (s, br, 3 F), −139.14 (d, $^3J_{F-F}$=23.7 Hz, 3 F), −139.35 (d, $^3J_{F-F}$=22.0 Hz, 3 F), −139.93 (d, $^3J_{F-F}$=21.2 Hz, 3 F), −155.79 (t, $^3J_{F-F}$=21.2 Hz, 3 F), −159.67 (t, $^3J_{F-F}$=22.3 Hz, 3 F), −163.28 (t, $^3J_{F-F}$=21.7 Hz, 3 F), −163.87 (t, $^3J_{F-F}$=22.6 Hz, 3 F), −164.13 (t, $^3J_{F-F}$=22.6 Hz, 3 F). $^{13}C$ NMR ($C_7D_8$, 23° C.): δ130.22 ($C_5Me_4$), 128.18 ($C_5Me_4$), 127.22 ($C_5Me_4$), 126.47 ($C_5Me_4$), 124.37 ($C_5Me_4$), 58.47 (N—$CMe_3$), 34.37 (Zr—$CH_3$), 34.10 (N—$CMe_3$), 15.89 ($C_5Me_4$), 13.46 ($C_5Me_4$), 11.77 ($C_5Me_4$), 10.99($C_5Me_4$), 7.92 ($SiMe_2$), 5.65 ($SiMe_2$). Anal. Calcd for $C_{53}H_{33}BF_{27}NSiZr$: C, 47.97; H, 2.51; N, 1.06; Found: C, 47.79; H, 2.58; N, 0.86.

EXAMPLE 8
Ethylene Polymerization

The reaction was conducted in a 250 mL flamed round bottom flask attached to a high vacuum line. The flask was equipped with a large magnetic stirring bar and a straight-bore high vacuum stopcock. The exterior connecting tube of the stopcock (Ca. 10 mm in length) is sealed with a new serum cap. The reaction vessel is then evacuated for several hours, back-filled with inert gas (Ar), the stopcock closed, and the reaction flask reevacuated. A measured amount of a nonpolar solvent such as benzene or toluene is vacuum transferred into the flask. Gaseous ethylene is admitted to the reaction flask through the purification column. The gas pressure is continuously maintained at 1 atm. Rapid stirring of the solution is initiated and after several minutes (to allow the saturation of the solvent with ethylene), the stopcock is opened and a small aliquot of catalyst solution (in the same solvent as used for the reaction) is injected by a gas-tight syringe just above the rapidly stirring solution through a serum cap (the syringe needle had been flattened so that the catalyst solution exits in a fine spray). Solid polyethylene is formed immediately. The reaction is quenched after a certain amount of time by injecting methanol through the serum cap on the stopcock. The solid polyethylene was collected by filtration, washed with methanol and then dried under vacuum at 100° C. Copolymerization may occur with the addition of a second monomer such as another α-olefin.

Ethylene polymerizations were carried out at room temperature in 250-mL flamed, round-bottom flasks attached to a high-vacuum line. In a typical experiment, a solution of each of the catalysts of Example 3 in 2 mL of toluene was quickly injected using a gas-tight syringe equipped with a spraying needle into respective rapidly stirred flasks containing 100 mL of toluene which was pre-saturated under 1 atm of rigorously purified ethylene. In the case of the catalysts prepared in Example 3, the catalyst solution was generated in situ by mixing $Cp_2ZrMe_2$ and PBB in 2 mL of toluene after aging for 0.5 h at 60° C., and then quickly injected into respective flasks under an ethylene atmosphere using a pre-warmed gas-tight syringe. The polymerization was quenched with acidic $CH_3OH$ after a short time period (10–60 s) at which point voluminous quantities of polyethylene precipitated out. The respective polymeric products were collected by filtration, washed with methanol and dried under high vacuum to a constant weight.

EXAMPLE 9
Ring-Opening Polymerization of THF

A small amount of [($C_5H_3Me_2$)$_2$(Me)Zr—Me—Zr(Me) ($C_5H_3Me_2$)$_2$]⁺ (MePBB)⁻ was loaded into a J-Young NMR tube and THF-$d_8$ was then vacuum-transferred into the tube. The mixture was slowly warmed to room temperature and left for several hours. The solid polymer formed in the tube was shown to be polytetrahydrofuran by $^1H$ analysis.

EXAMPLE 10
Propylene Polymerization

This reaction is carried out in a 100 mL quartz Worden vessel equipped with a magnetic stirring bar, a pressure gauge and a stainless steel o-ring assembly attached to a high vacuum line. In a typical experiment, the reaction vessel is flamed and then pumped under high vacuum for several hours, filled with inert gas and brought into a glove box. A measured amount of catalyst is added into the vessel. On the high vacuum line, a measured amount of the solvent and propylene are condensed in at −78° C. The reaction apparatus is sealed off and warmed to the desired temperature. During the polymerization process, the reaction tube is immersed in a large amount of tap water (20–25° C.) or ice water (0° C.) to help dissipate the heat produced from the polymerization and keep the temperature constant. The progress of the polymerization reactions is monitored through observance of the pressure change. After the reaction is finished (pressure drops to zero psi), the resulting oily liquid is removed from the vessel, washed with methanol and water and dried under vacuum at 90–100° C. for ten hours to result in a colorless oil.

Table II sets forth the relevant data concerning propylene polymerization utilizing the catalyst prepared according to the enumerated example.

TABLE II

| Example | 3 | 5 |
|---|---|---|
| Metallocene Cation/Anion* | ($Cp_2ZrMe$)$_2Me$⁺/(MePBB)⁻ | ($Cp_2ZrMe$⁺)/(MePBB)⁻ |
| Catalyst (mM) | 0.15 | 0.15 |
| Reaction Time (m) | 40 | 40 |
| Yield (g) | 4.0 | 5.0 |

*Cp = $C_5H_5$

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

That which is claimed is:

1. A catalytic complex selected from the group consisting of:
A) a complex of the formula [CpCp'MMe($\mu$-Me)MeMCpCp']$^\oplus$[MeBR'R"$_2$]$^\ominus$
B) a complex of the formula [CpCp'MH($\mu$-H)HMCpCp']$^\oplus$[MeBR'R"$_2$]$^\ominus$
C) a complex of the formula [CpMMe$_2$]$^\oplus$[MeBR'R"$_2$]$^\ominus$
D) a complex of the formula [C$_5$H$_m$R$_{4-m}$XNRMMe]$^\oplus$[MeBR'R"$_2$]$^\ominus$
E) a complex of the formula [CpCp'MMe]$^\oplus$[MeBR'R"$_2$]$^\ominus$
where:
Cp and Cp' each is C$_5$H$_n$R$_{5-n}$ where n is 0–5, or indenyl;
R is an alkyl or benzyl or aryl or silyl group, each having 20 or less carbon atoms;
M is Th, Zr, Hf, or Ti;
Me is methyl;
B is boron;
H is hydrogen;
R' is fluorinated biphenyl;
R" is a fluorinated phenyl, fluorinated biphenyl, or fluorinated polycyclic fused ring group;
m is 0–4;
X is R'''$_2$Si, R''' being alkyl or aryl, either one having 10 or less carbon atoms; and
N is nitrogen.

2. A catalytic complex of claim 1 of the formula

[CpCp'MMe($\mu$-Me)MeMCpCp']$^\oplus$[MeBR'R"$_2$]$^\ominus$ where
each of Cp and Cp' is C$_5$H$_n$R$_{5-n}$ and n is 0–5;
R is alkyl or benzyl or aryl, each of 20 or less carbon atoms;
M is Th, Zr, Hf, or Ti;
Me is methyl;
B is boron;
R' is fluorinated biphenyl; and
R" is a fluorinated phenyl, fluorinated biphenyl, or fluorinated polycyclic fused ring group.

3. A complex of claim 2 wherein each R" is fluorinated biphenyl.

4. A complex of claim 2 wherein R' is nonafluorobiphenyl, and wherein each R" is nonafluorobiphenyl.

5. A complex of claim 3 wherein each of Cp and Cp' is $\eta^5$-cyclopentadienyl, $\eta^5$-dimethylcyclopentadienyl, or $\eta^5$-pentamethylcyclopentadienyl.

6. A complex of claim 4 of the formula

7. A complex of claim 4 of the formula

8. A complex of claim 4 of the formula

9. A catalytic complex of claim 1 of the formula

[CpCp'MH($\mu$-H)HMCpCp']$^\oplus$[MeBR'R"$_2$]$^\ominus$ where
each of Cp and Cp' is C$_5$H$_n$R$_{5-n}$ and n is 0–5;
R is alkyl or benzyl or aryl, each of 20 or less carbon atoms;
M is a Th, Zr, Hf, or Ti;
H is a hydrogen atom;
B is boron;
R' is fluorinated biphenyl; and
R" is a fluorinated phenyl, fluorinated biphenyl, or fluorinated polycyclic fused ring group.

10. A complex of claim 9 wherein each R" is fluorinated biphenyl.

11. A complex of claim 9 wherein R' is nonafluorobiphenyl, and wherein each R" is nonafluorobiphenyl.

12. A complex of claim 11 wherein each of Cp and Cp' is $\eta^5$-cyclopentadienyl or $\eta^5$-dimethylcyclopentadienyl.

13. A complex of claim 11 of the formula

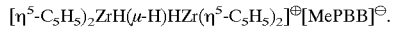

14. A complex of claim 11 of the formula

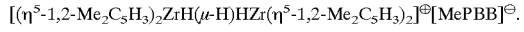

15. A catalytic complex of claim 1 of the formula

[CpMMe$_2$]$^\oplus$[MeBR'R"$_2$]$^\ominus$ where
Cp is C$_5$H$_n$R$_{5-n}$ and n is 0–5;
R is alkyl, benzyl or aryl, each of 20 or less carbon atoms;
M is Th, Zr, Hf, or Ti;
Me is methyl;
B is boron;
R' is fluorinated biphenyl; and
R" is a fluorinated phenyl, fluorinated biphenyl, or fluorinated polycyclic fused ring group.

16. A complex of claim 15 wherein each R" is fluorinated biphenyl.

17. A complex of claim 15 wherein R' is nonafluorobiphenyl, and wherein each R" is nonafluorobiphenyl.

18. A complex of claim 16 wherein Cp is $\eta^5$-cyclopentadienyl, $\eta^5$-dimethylcyclopentadienyl, or $\eta^5$-pentamethylcyclopentadienyl.

19. A complex of claim 17 of the formula

20. A complex of claim 17 of the formula

21. A complex of claim 17 of the formula

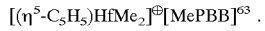

22. A complex of claim 17 of the formula

[($\eta^5$-Me$_2$C$_5$H$_3$)HfMe$_2$]$^\oplus$[MePBB]$^\ominus$.

23. A complex of claim 17 of the formula

[($\eta^5$-Me$_2$C$_5$H$_3$)TiMe$_2$]$^\oplus$[MePBB]$^\ominus$.

24. A complex of claim 17 of the formula

[($\eta^5$-Me$_5$C$_5$)ZrMe$_2$]$^\oplus$[MePBB]$^\ominus$.

25. A complex of claim 17 of the formula

[($\eta^5$-Me$_5$C$_5$)HfMe$_2$]$^\oplus$[MePBB]$^\ominus$.

26. A catalytic complex of claim 1 of the formula

[C$_5$H$_m$R$_{4-m}$XNRMMe]$^\oplus$[MeBR'R''$_2$]$^\ominus$ where
m is 0–4;
R is alkyl, benzyl or aryl, each of 20 or less carbon atoms;
X is R'''$_2$Si, R''' being alkyl or aryl, either one having 10 or less carbon atoms;
M is Th, Zr, Hf, or Ti;
N is nitrogen;
Me is methyl;
B is boron;
R' is fluorinated biphenyl; and
R'' is a fluorinated phenyl, fluorinated biphenyl, or fluorinated polycyclic fused ring group.

27. A complex of claim 26 wherein each R'' is fluorinated biphenyl.

28. A complex of claim 26 wherein R' is nonafluorobiphenyl, and wherein each R'' is nonafluorobiphenyl.

29. A complex of claim 26 wherein M is Zr.

30. A complex of claim 26 wherein M is Ti.

31. A complex of claim 26 of the formula

[Me$_2$Si($^t$BuN)(C$_5$Me$_4$)ZrMe]$^\oplus$[MeBR'R''$_2$]$^\ominus$

32. A complex of claim 26 of the formula

[Me$_2$Si($^t$BuN)(C$_5$Me$_4$)TiMe]$^\oplus$[MeBR'R''$_2$]$^\ominus$

33. A catalytic complex of claim 1 of the formula

[CpCp'MMe]$^\oplus$[MeBR'R''$_2$]$^\ominus$ where
each of Cp and Cp' is C$_5$H$_n$R$_{5-n}$ is 0–5, or indenyl;
R is alkyl or benzyl or aryl, each of 20 or less carbon atoms;
M is Th, Zr, Hf, or Ti;
Me is methyl;
B is boron;
R' is fluorinated biphenyl; and
R'' is a fluorinated phenyl, fluorinated biphenyl, or fluorinated polycyclic fused ring group.

34. A complex of claim 33 wherein each R'' is fluorinated biphenyl.

35. A complex of claim 33 wherein R' is nonafluorobiphenyl, and wherein each R'' is nonafluorobiphenyl.

36. A complex of claim 33 wherein each of Cp and Cp' is $\eta^5$-cyclopentadienyl or $\eta^5$-dimethylcyclopentadienyl or $\eta^5$-pentamethylcyclopentadienyl.

37. A complex of claim 33 of the formula

[($\eta^5$-C$_5$H$_5$)$_2$ZrMe]$^\oplus$[MePBB]$^\ominus$.

38. A complex of claim 33 of the formula

[($\eta^5$-1,2-Me$_2$C$_5$H$_3$)$_2$ZrMe]$^\oplus$[MePBB]$^\ominus$.

39. A complex of claim 33 of the formula

[($\eta^5$-Me$_5$C$_5$)$_2$ZrMe]$^\oplus$[MePBB]$^\ominus$.

40. A complex of claim 33 of the formula

[($\eta^5$-Me$_5$C$_5$)$_2$ThMe]$^\oplus$[MePBB]$^\ominus$.

* * * * *

UNITED STATES PATENT AND TRADEMARK OFFICE
CERTIFICATE OF CORRECTION

PATENT NO. : 6,274,752 B1
DATED : August 14, 2001
INVENTOR(S) : Tobin J. Marks et al.

It is certified that error appears in the above-identified patent and that said Letters Patent is hereby corrected as shown below:

Column 11, claim 5,
Line 65, reads "$^5$-pentamethylcyclopentadienyl" and should read -- $\eta^5$-pentamethylcyclopentadienyl --.

Column 12, claim 7,
Line 3, reads "$[\eta^5\text{-}1,2\text{-}Me_2C_5H_3)_2ZrMe(\mu\text{-}Me)MeZr(\eta^5\text{-}1,2\text{-}Me_2C_5H_3)_2]^{\oplus}[MePBB]^{\ominus}$" and should read -- $[(\eta^5\text{-}1,2\text{-}Me_2C_5H_3)_2ZrMe(\mu\text{-}Me)MeZr(\eta^5\text{-}1,2\text{-}Me_2C_5H_3)_2]^{\oplus}[MePBB]^{\ominus}$ --.

Column 12, claim 8,
Line 7, last part of formula reads "$[(\eta^5\text{-}Me_5C_5)_2ZrMe(\mu Me)MeZr(\eta^5\text{-}Me_5C_5)_2]^{\oplus}[MePBB]^{\oplus}$" and should read -- $[(\eta^5\text{-}Me_5C_5)_2ZrMe(\mu\text{-}Me)MeZr(\eta^5\text{-}Me_5C_5)_2]^{\oplus}[MePBB]^{\ominus}$ --.

Column 12, claim 13,
Line 32, reads "$[\eta^5 C_5H_5)_2ZrH(\mu\text{-}H)HZr(\eta^5\text{-}C_5H_5)_2]^{\oplus}[MePBB]^{\ominus}$" and should read -- $[(\eta^5\text{-}C_5H_5)_2ZrH(\mu\text{-}H)HZr(\eta^5\text{-}C_5H_5)_2]^{\oplus}[MePBB]^{\ominus}$ --.

Column 12, claim 21,
Line 66, reads "$[(\eta^5\text{-}C_5H_5)HfMe_2]^{\oplus}[MePBB]^{63}$" and should read -- $[(\eta^5\text{-}C_5H_5)HfMe_2]^{\oplus}[MePBB]^{\ominus}$ --.

UNITED STATES PATENT AND TRADEMARK OFFICE
CERTIFICATE OF CORRECTION

PATENT NO. : 6,274,752 B1
DATED : August 14, 2001
INVENTOR(S) : Tobin J. Marks et al.

It is certified that error appears in the above-identified patent and that said Letters Patent is hereby corrected as shown below:

<u>Column 14, claim 33,</u>
Line 9, reads "$C_5H_nR_{5-n}$ is" and should read -- $C_5H_nR_{5-n}$ and n is --.

Signed and Sealed this

Ninth Day of April, 2002

*Attest:*

JAMES E. ROGAN
*Attesting Officer*   *Director of the United States Patent and Trademark Office*